| United States Patent [19] | [11] Patent Number: 5,017,491 |
| Freyssinet et al. | [45] Date of Patent: May 21, 1991 |

[54] PROCESS FOR REGENERATING SUNFLOWERS BY EMBRYOGENESIS

[75] Inventors: Georges Freyssinet; Martine Freyssinet, both of St Cyr Au Mont d'Or, France

[73] Assignee: Rhone-Poulenc Agrochimie, Lyons, France

[21] Appl. No.: 115,055

[22] Filed: Oct. 30, 1987

[30]  Foreign Application Priority Data

Oct. 30, 1986 [FR] France ................................ 86 15299

[51] Int. Cl.$^5$ .............................................. C12N 5/00
[52] U.S. Cl. ............................ 435/240.5; 435/240.49; 435/240.54
[58] Field of Search ........... 435/240.49, 240.5, 240.54; 800/1

[56]  References Cited

U.S. PATENT DOCUMENTS 4,670,391  6/1987  Cooley et al. .................. 435/240.49

OTHER PUBLICATIONS

Greco et al., 1984, Plant Science Letters 36: 73-77.

*Primary Examiner*—Elizabeth C. Weimar
*Assistant Examiner*—David T. Fox
*Attorney, Agent, or Firm*—Burns, Doane, Swecker & Mathis

[57]  ABSTRACT

Process for regenerating cultivars from immature embryos.

It comprises three stages:
  formation of embryogenic calluses in a medium containing a hormone of the cytokinin type,
  culturing the calluses in a medium of the same nature as above,
  culturing the plantlets.

Application to sunflower cultivars.

12 Claims, No Drawings

PROCESS FOR REGENERATING SUNFLOWERS BY EMBRYOGENESIS

The present invention relates to a process for regenerating sunflower plants, from cells or tissues, by somatic embryogenesis. The present invention also relates to the sunflower plants and seeds produced by this method.

Although it is possible to regenerate plants from isolated cells or from tissues of a large number of cultivated species, efforts with the sunflower (*Helianthus annuus*) have often been fruitless. A few methods are described in the literature, relating to the regeneration of sunflowers by somatic embryogenesis, but these methods relate only to rare genotypes or to interspecific hybrids. Explants are cultured on a first medium which induces the formation of a callus. The callus is then transferred to a second medium which induces the formation of somatic embryos and plantlets. The plantlets are then transferred to a third medium which induces the formation of roots, and at this stage, the regenerated plants can be planted in the soil.

PATERSON and EVERETT (Plant Sci., 1985, 42, 125) have developed a medium, an optimization of that of GEORGIEVA-TODOROVA et al (Proc. 9th Int. Sunflower Conference, Torremolinos, Spain, 1980, 122), which induces the regeneration of a cultivated species of sunflower, SS 415 B, by somatic embryogenesis from hypocotyl fragments. The explants are cultured in darkness for 2 weeks, and then in the light for 2–4 weeks on a modified Murasnige and Skoog (MS) medium, supplemented with 40 mg/l of adenine sulphate, 1 mg/l of 6-benzylaminopurine (BAP), 1 mg/l of naphthaleneacetic acid (NAA) and 0.1 mg/l of gibberellin (GA3). During the first 2 weeks, a friable callus forms, and then green spots are seen to appear in the light, these transforming into shoots. An anatomical study reveals that these green spots are somatic embryos similar to the zygotic embryos.

CHANDLER and JAN (Agronomy Abstr., 1983, 58) describe the regeneration of sunflowers from immature embryos derived from interspecific crosses. The immature embryos (4 to 5 days) are placed on the growth medium described by CHANDLER and BEARD for the salvage of embryos (Crop. Sci., 1983, 23, 1004). After 2 to 3 weeks, the embryos which have enlarged are transferred to different formulations based on MS medium, with variable doses of auxin and cytokinin. The production of plants on these media follows various routes, including direct germination or callus induction followed by organogenesis or embryogenesis. The best results are obtained with concentrations of indoleacetic acid (IAA) and kinetin of between 0 and 1 ppm. The advantage of this system is the multiple production of clones from a single embryo.

COOLEY and WILCOX (European Patent Application 0172377) propose a process applied to sunflower cultivars HA 89 and RHA 274, comprising the three stages described above and performed on three different culture media, the culture media of the first two stages necessarily containing a hormone of the auxin type. However, this process has several disadvantages, on the one hand of being applicable to embryos whose size falls within a narrow range (from 0.1 to 2 mm) there hence being little flexibility, on the other hand of necessitating a change of medium between the first and the second stage, and finally in that the degree of regeneration of the plantlets that is obtained still remains very indadequate.

The present invention relates to a simpler process for regenerating sunflower cultivars, leading to plantlets having an improved capacity for growing again as a soil crop.

More especially, it relates to a process for regenerating sunflower cultivars from immature embryos, comprising successively:

a first stage of formation of embryogenic calluses from cells or tissues by culturing in a nutrient induction medium containing a hormone;

a second stage of culturing the embryogenic calluses for their growth, their development and their germination in a medium containing a hormone;

an optional a third stage consisting of a culturing which permits the growth and development of plants;

wherein the first two stages are performed on a medium of the same nature and wherein this medium contains an effective quantity of a hormone of the cytokinin type without auxinic type hormone.

In the following description, the percentages are given in weight/volume, unless otherwise indicated.

The plant tissues from which explants may be taken for the production of somatic embryos originate from cultivars of sunflower *Helianthus annuus* used essentially in selection programmes. The process is exemplified using eight cultivars: HA 89, HA 290, HA 291, HA 300, HA 303, T 76, RT 26 and Giant Gray Stripe. The variety HA 89 comes from Dade Counts, Fla., the varieties HA 290, HA 291, HA 300, HA 303, T 76 and RT 26 from Seedtec International Inc., Woodland, California and the Giant Gray Stripe from Northrup King Seeds, Fresno, Calif.

The explants are derived from plants cultivated in the greenhouse and subjected to controlled fertilization. The preferred explant for the production of calluses is the immature embryo. The immature embryos with pericarps are isolated from the sunflower capitula when they are from 4 to 21 days old; their size is generally between 0.1 and 5 mm. The large-sized immature embryos can be cut into several equal portions according to planes passing through the gemmule-radicle axis, thereby multiplying the number of clones obtained from a single embryo.

The process according to the invention is carried out in the following manner:

Sunflower varieties HA 89, HA 290, HA 291, HA 300, HA 303, T 76, RT 26 and Giant Gray Stripe are cultivated in the greenhouse (26° C., 40,000 lux, 15-h photoperiod per day) and subjected to a controlled fertilization. The immature embryos are removed 4 to 21 days after pollination. The seeds detached from the capitula are sterilized by immersion for 20 minutes in a solution of commercial Javelle water having a chlorometric strength of 3°, to which have been added a few drops of a Tween 80 wetting agent, a condensate of ethylene oxide (8–10 moles) with nonylphenol, and then washed 3 times with sterile distilled water. The embryos are then isolated under aseptic conditions, cut up if appropriate and deposited on the first, so-called embryo induction medium.

This first medium comprises inorganic salts, vitamins, amino acids, sucrose and a hormone in sufficient quantity for the formation of calluses. The inorganic salts comprise salts of macroelements and salts of trace elements. The macroelements used in this first medium can be chosen, e.g., from the following compounds: magnesium sulphate, calcium chloride, monopotassium phosphate, potassium nitrate and ammonium nitrate. Among the salts based on trace elements, there may be mentioned boric acid, manganese sulphate, zinc sulphate, sodium molybdate, cupric sulphate, cobalt chloride, potassium iodide and iron Na EDTA chelate. This combination of organic salts is known under the name of Murashige and Skoog (MS).

The preferred quantities of macroelements and trace elements for one liter of medium are as follows:
magnesium sulphate heptahydrate (370 mg),
calcium chloride dihydrate (440 mg),
monopotassium phosphate dihydrate (170 mg),
potassium nitrate (1,900 mg),
ammonium nitrate (1,650 mg),
boric acid (6.2 mg),
manganese sulphate tetrahydrate (22.3 mg),
zinc sulphate heptahydrate (8.6 mg),
sodium molybdate dihydrate (0.25 mg),
cupric sulphate pentahydrate (0.025 mg),
cobalt chloride hexahydrate (0.025 mg),
potassium iodide (0.83 mg), and
iron Na EDTA chelate (36.7 mg).

The first medium also contains vitamins such as nicotinic acid, thiamine, pyridoxine, myo-inositol and an amino acid such as alanine, glutamine, serine, tryptophan, cysteine and preferably glycine. The preferred quantities of vitamins and amino acid for one liter of medium are:
nicotinic acid (0.5 mg),
thiamine hydrochloride (0.1 mg),
myo-inositol (100 mg), and
glycine (2 mg).

The first medium can also contain a vitamin and amino acid supplement; this supplement is not essential to the formation of the somatic embryos, but it increases their frequency of occurrence. In this eventuality, the preferred quantities of vitamins and amino acids for 1 liter of medium will be:
nicotinic acid (0.5 mg),
thiamine hydrochloride (0.1 mg),
pyridoxine hydrochloride (0.5 mg),
myo-inositol (4,000 mg),
L-alanine (1,000 mg),
L-glutamine (800 mg),
L-serine (160 mg),
L-tryptophan (50 mg),
L-cysteine (10 mg), and
glycine (2 mg).

The sucrose contained in the first medium is present in the proportion of 8 to 12%, and preferably 9%.

The hormone of the first medium, the choice of which is a characteristic of the invention, is of the cytokinin type, e.g. kinetin or 6-benzylaminopurine, and preferably the latter. In general, quantities from 0.5 to 1 mg per liter of medium are suitable. An agar such as Phytagar or Gelrite is used in order to make the medium solid. A final concentration of 0.6% for Phytagar or 0.3% for Gelrite gives good results. The pH of the medium can vary from 5.0 to 6.3 and is preferably 5.0.

The medium is sterilized in the autoclave, with the exception of the hormones which are sterilized by filtration through a microporous membrane.

The immature embryos, deposited on this first medium, are cultured for approximately 2 to 3 weeks in darkness at 26° C. During this period, the zygotic embryos develop and somatic embryos appear on the hypocotyl and on the inner face of the cotyledons in the case of the cultivar HA 291. These somatic embryos can then be isolated and deposited on the second, so-called plantlet growth medium. The embryogenic callus or the isolated embryos are cultured on the second medium for 2 to 3 weeks at 26° C. in the light (1,500 lux) with a photoperiod of 12 to 16 h per day, and preferably 16 h per day. During this period, the embryos germinate and the plantlets formed possibly develop roots.

The second medium contains, like the first medium, inorganic salts, vitamins, an amino acid, sucrose and a hormone. The inorganic salts comprise salts of macroelements and salts of trace elements. The macroelements, trace elements, vitamins and amino acid are the same as in the first medium, in identical concentrations without supplementation. The sucrose is preferably present in a smaller quantity than in the first medium, e.g. from 2 to 4%, and preferably 3%. The hormone used is a cytokinin, preferably identical to (but capable of being different from) that of the first medium, and preferably 6-benzylaminopurine. In general, quantities from 0.1 to 0.5 mg per liter are suitable. An agar such as Phytagar or Gelrite is used in order to make the medium solid. A final concentration of 0.6% for Phytagar and 0.3% for Gelrite gives good results. The medium is sterilized as above, and has a pH of 5.0 to 6.3, with a preference for a pH of 5.0.

After 2 to 3 weeks on the second medium, the isolated somatic embryos have germinated and have been transformed to plantlets measuring 2 to 5 cm. The plantlets which have developed roots can be moved to soil, in a sterile mixture of peat, vermiculite and fine sand (3:2:1) contained in Jiffy-pots; the pots are placed in a trough filled with wet sand and are covered with a transparent polyethylene bag so as to maintain a high degree of humidity. The whole arrangement is placed in a climatic chamber at 15° C. (6,000 lux) with a photoperiod of 12 to 16 h per day, and preferably 15 h per day. After 10 days, the plants are moved to larger pots and cultivated in the greenhouse at 26° C. (40,000 lux) with a photoperiod of 12 to 16 h per day, and preferably 15 h per day.

The plants which have not developed roots can be either grafted onto young plants cultivated in the greenhouse according to a traditional method (see, e.g. HABERMANN and WALLACE, Amer. J. Bot., 1958, 45, 479), or transferred for a period of 10 to 20 days to a rooting medium or third medium.

The third medium comprises inorganic salts, vitamins and sucrose. The inorganic salts comprise salts of macroelements and salts of trace elements. The macroelements used in this third medium can be chosen from the following compounds: magnesium sulphate, calcium chloride, monosodium phosphate, potassium nitrate and ammonium sulphate. Among the salts based on trace elements, there may be mentioned boric acid, manganese sulphate, zinc sulphate, sodium molybdate, cupric sulphate, cobalt chloride, potassium iodide and iron Na EDTA chelate. This combination of inorganic salts is known under the name B5. The preferred quantities of macroelements and trace elements for one liter of medium are as follows:
magnesium sulphate heptahydrate (250 mg),
calcium chloride dihydrate (150 mg),
monosodium phosphate monohydrate (169 mg),
potassium nitrate (3,000 mg),
boric acid (3 mg),
manganese sulphate tetrahydrate (13.2 mg), zinc sulphate heptahydrate (2 mg),
sodium molybdate dihydrate (0.25 mg),
cupric sulphate pentahydrate (0.025 mg),
cobalt chloride hexahydrate (0.025 mg),
potassium iodide (0.75 mg), and
iron Na EDTA chelate (40 mg).

The third medium also contains vitamins. These are nicotinic acid, thiamine, pyridoxine and myo-inositol. The preferred quantities of vitamins are, for one liter of medium:
nicotinic acid (1 mg),
thiamine hydrochloride (10 mg),
pyridoxine hydrochloride (1 mg), and
myo-inositol (100 mg).

The third medium also contains sucrose, and activated charcoal or a hormone of the auxin type. The sucrose is present, e.g. in the proportion of 1 to 2%, and preferably 1%, and the activated charcoal in the proportion of 0.1%. If the use of a hormone is preferred in place of activated charcoal, 3-indoleacetic acid at doses of 0.1 to 0.2 mg per liter will be selected. An agar such as Phytagar or Gelrite is used in order to make the medium solid. A final concentration of 0.5% for Phytagar and 0.25% for Gelrite is sufficient. The pH of the medium can vary from 5.0 to 6.0 and is preferably 5.0. The medium is sterilized in the autoclave.

The plants are cultured on this medium for 2 to 3 weeks at 26° C. in the light (1,500 lux), with a photoperiod of 12 to 16 h per day, and preferably 16 h per day. The plants then form roots and can be moved to soil.

The plants obtained by this process can be phenotypically different from the starting material, on account of the in vitro stress. The plants are manually pollinated and stored until the seeds are harvested. A few of the seeds are planted for the analysis of new sunflower plants and the possible selection of advantageous mutants, which are then integrated in a variety selection programme.

The present invention will be described more completely, but without limitation, in the examples below:

EXAMPLE I

Preparation of the stock solutions (a) Stock solution of B5

A stock solution of B5, concentrated 10-fold, is prepared by dissolving a sachet of B5 medium without sucrose from Flow Laboratories [contains the inorganic salts of B5, nicotinic acid (1 mg), pyridoxine HCl (1 mg), thiamine HCl (10 mg) and inositol (100 mg), final concentrations] in distilled and deionized water (1,000 cc final volume). The stock solution is divided into 100-cc aliquots and stored at −20° C.

(b) Stock solution of BAP

A solution of BAP containing 1 g/l is prepared by dissolving 6-benzylaminopurine (100 mg) in 0.15 N HCl (a few cc), heated gently and diluting to 100 cc with distilled and deionized water. This solution is sterilized by filtration through a 0.2 micron Minisart NML membrane (Sartorius) before being added to the first and second media.

(c) Stock solution of IAA

A solution of IAA containing 0.2 g/l is prepared by dissolving 3-indole acetic acid (20 mg) in pure ethanol (a few cc), and diluting to 100 cc with distilled and deionized water. This solution is sterilized by filtration through a 0.2 micron Minisart NML membrane (Sartorius) before being added to the third medium.

(d) Vitamin and amino acid supplement according to CHANDLER and BEARD (Crop. Sci., 1983), 23, 1004)

A stock solution of vitamin and amino acids, concentrated 20-fold, is prepared by dissolving together myo-inositol (39 g), L-alanine (10 g), L-glutamine (8 g), L-serine (1.6 g), L-tryptophan (0.5 g) and L-cysteine (0.1 g) in distilled and deionized water (500 cc final volume). The stock solution is divided into 50-cc aliquot portions and stored at −20° C.

EXAMPLE II

Preparation of the media (a) First medium or embryo induction medium

This is prepared by dissolving a sachet of Murashige and Skoog medium without sucrose from Flow Laboratories [contains the inorganic salts of MS, thiamine HCl (0.1 mg), nicotinic acid (0.5 mg), pyridoxine HCl (0.5 mg), glycine (2 mg) and inositol (100 mg)] and sucrose (90 to 120 g) in distilled and deionized water. After the optional addition of the vitamin and amino acid supplement (500 cc), the pH is adjusted to 5.0 with 0.1 N caustic soda, the volume brought to 1 liter and, after the addition of Phytagar (6 g, Gibco) or Gelrite (3 g, Kelco), the mixture is autoclaved for 20 minutes at 120 psi. When the medium is lukewarm, the BAP solution (2.2–4.4 μM; 0.5 to 1 cc), sterilized as described above, is added to it. The mixture is then poured into Petri dishes.

(b) Second medium or plantlet growth medium.

The second medium is prepared in an identical manner to the first medium, by dissolving together a sachet of MS medium, sucrose (30 g) and Phytagar (6 g) or Gelrite (3 g) in one liter of water and adding, after autoclaving, the sterile BAP solution (0.44–2.2 μM; 0.1 to 0.5 cc). The medium is poured into Plantcon dishes (Flow Laboratories).

(c) Third medium or rooting medium

The third medium is prepared by adding sucrose (10 to 20 g) to the stock solution (100 cc) of B5 in distilled and deionized water. The pH is adjusted to 5.0 with 0.1 N caustic soda, then the volume is brought to 1 liter and Phytagar (5 g) and activated charcoal (1 g) are added to the mixture. After autoclaving, the medium is poured into Mason jars. If it is desired to use a third medium containing IAA, the activated charcoal is omitted during the preparation of this third medium. After autoclaving, the sterile IAA solution (0.57–1.14 μM; 0.5 to 1 cc) is added to the lukewarm medium. The medium is poured in an identical manner into Mason jars.

A liquid variant of the third medium comprises only the inorganic salts of B5 and 1% of sucrose, at pH 5.0. The mixture is distributed in 10-ml portions into glass tubes containing filter paper bridges, according to the method described by CHANDLER and BEARD (Crop Sci., 1983, 23, 1004), and then autoclaved.

EXAMPLE III

The immature embryos with their pericarps are separated from the sunflower (*Helianthus annuus*, var. T 76 B) capitulum when they reach 0.5 to 1.5 mm. The seeds are sterilized for 20 minutes in a solution of Javelle water having a chlorometric strength of 3 degrees, and rinsed with distilled water. The immature embryos are separated from their coats and deposited in Petri dishes on the first medium. The first medium is prepared in the manner described above, with sucrose (90 g/l) and BAP (0.5 mg/l, 2.2 μM).

The Petri dishes are incubated in darkness for 3 weeks in order to induce the formation of somatic embryos.

At this stage, the somatic embryos which have begun to germinate are separated from the zygotic embryo and deposited on the second medium, in Plantcon dishes. The second medium, prepared as described above, contains 0.1 mg of BAP per liter, equivalent to 0.44 μM. The embryos are cultured in the light for 3 weeks, and differentiate to plantlets.

The plantlets, 2 to 5 cm in height, are then transferred to the third medium in order to initiate root formation. The third medium, prepared as described above, preferably contains 10 g of sucrose. In the case of the gelled medium, the addition of activated charcoal (1 g/l) abolishes the residual influence of the BAP supplied by the preceding medium (MAENE and DEBERGH, Plant Cell Tissue Organ Culture, 1985, 5 23-33) and promotes rapid growth of the roots. After approximately 2 weeks, the plantlets may be moved to soil.

If the plantlets have begun to develop roots on the second medium, they may be placed in contact with the third liquid medium, according to the technique described by CHANDLER and BEARD (Crop Sci. 1983, 23, 1004). This arrangement permits a substantial development of the root system, and avoids damage to the roots when the plants are moved to soil.

EXAMPLE IV

The immature embryos of *Helianthus annuus*, var. HA 89, are removed when they reach 0.1 to 0.5 mm and arranged, with the endosperm, on the first medium. The first medium contains sucrose (90 g per liter) and BAP (0.5 mg per liter, equivalent to 2.2 μM). After 3 weeks in darkness, the somatic embryos are isolated and deposited on the first fresh medium, still in darkness. Secondary somatic embryos will form on the isolated embryos. After 3 weeks in darkness, the secondary somatic embryos are isolated and deposited on the second medium. The second medium contains sucrose (30 g per liter) and BAP (0.1 mg per liter, (0.44 μM).

The plantlets which will develop may then be transferred to the third medium, liquid or gelled, in order to root. They will then be moved to soil.

EXAMPLE V

The immature embryos of *Helianthus annuus*, var. HA 89, are removed 21 days after pollination; they are 5 mm in size. They are separated from their coats and, before being deposited on the first medium, they are cut longitudinally into four equal portions according to two planes perpendicular to one another and parallel to the gemmule-radicle axis. In this case, the first medium contains sucrose (90 g per liter) and BAP (1 mg per liter). After 3 weeks in darkness, the somatic embryos are isolated and deposited on the second medium. The second medium contains sucrose (30 g per liter) and BAP (0.5 mg per liter).

The plantlets which will develop may then be transferred to the third medium (liquid or gelled) in order to root, and then moved to soil. The plantlets which have not produced roots may be grafted onto a young plant according to the method described by HABERMANN and WALLACE (Amer. J. Bot., 1958, 45, 479).

EXAMPLES 6-27

The examples below give a non-exhaustive idea of the combinations which may be carried out using the different procedures described.

| Example | Variety | Size (mm) | Sections | Medium I Parent medium | Medium I Sucrose % | Medium I BAP mg/l | Medium II Parent medium | Medium II Sucrose % | Medium II BAP mg/l | Rooting |
|---|---|---|---|---|---|---|---|---|---|---|
| 6 | T 76 | 1.5 | — | modMS* | 9 | 1 | modMS* | 3 | 1 | modMS* + 3% sucrose + 0.5 BAP |
| 7 | T 76 | 1.5 | — | modMS* | 9 | 1 | modMS* | 3 | 1 | III SC |
| 8 | T 76 | 1.5 | — | modMS* | 9 | 1 | modMS* | 3 | 1 | III L |
| 9 | T 76 | 1.5 | — | MS | 9 | 1 | MS | 3 | 1 | III SC |
| 10 | T 76 | 1.5 | — | MS | 12 | 0.5 | MS | 3 | 0.1 | III SC |
| 11 | T 76 | 1.5 | — | MS | 12 | 0.5 | MS | 3 | 0.1 | III L |
| 12 | T 76 | 1.5 | — | supMS** | 9 | 0.5 | MS | 3 | 0.1 | III SA 0.1 |
| 13 | T 76 | ≦3 | — | MS | 9 | 0.5 | MS | 3 | 0.5 | III SC |
| 14 | T 76 | ≦3 | — | MS | 9 | 0.5 | MS | 3 | 0.5 | III L |
| 15 | T 76 | =5 | + | MS | 9 | 0.5 | MS | 3 | 0.5 | III SC |
| 16 | T 76 | =5 | + | MS | 9 | 0.5 | MS | 3 | 0.5 | III L |
| 17 | RT 26 | ≦1.5 | — | MS | 12 | 0.5 | MS | 3 | 0.1 | III L |
| 18 | RT 26 | ≦3 | — | supMS** | 9 | 0.5 | MS | 3 | 0.1 | III SC |
| 19 | HA 89 | ≦1.5 | — | MS | 12 | 0.5 | MS | 3 | 0.5 | III SC |
| 20 | HA 89 | ≦3 | — | MS | 9 | 0.5 | MS | 3 | 0.5 | III SC |
| 21 | HA 89 | ≦3 | — | MS | 9 | 0.5 | MS | 3 | 0.5 | III L |
| 22 | HA 89 | ≦3 | — | supMS** | 9 | 0.5 | MS | 3 | 0.1 | III SC |
| 23 | HA 89 | =5 | + | MS | 9 | 0.5 | MS | 3 | 0.5 | III SC |
| 24 | HA 89 | =5 | + | MS | 9 | 0.5 | MS | 3 | 0.5 | III L |
| 25 | HA 89 | >5 | + | MS | 9 | 1 | MS | 3 | 0.5 | III SC |
| 26 | HA 291 | ≦1.5 | — | supMS** | 9 | 0.5 | MS | 3 | 0.1 | III SA 0.1 |
| 27 | HA 291 | =5 | + | supMS** | 9 | 0.5 | MS | 3 | 0.1 | III SA 0.2 |

*The modified MS medium contains calcium chloride dihydrate (600 mg), potassium nitrate (1,260 mg), ammonium nitrate (1,100 mg) and myo-inositol (250 mg) per liter of medium. The other constituents remain unchanged.
**supplemented MS medium
III SA = solid medium III + IAA (0.1 or 0.2 mg/l)
III SC = solid medium III + activated charcoal
III L = liquid medium III

We claim:
1. A process for regenerating cultivars of sunflower plants from *Helianthus annuus* by somatic embryogenesis comprising the steps of: (a) culturing immature em- bryos of sunflower plants in a nutrient induction medium containing from 2.2-4.4 μm of 6-benzylaminopurine to form embryogenic calluses and somatic embryos, and between 8%-12% of sucrose, (b) further culturing said embryos on a plantlet growth medium containing 0.44-4.4 μm of 6-benzylaminopurine to permit germination of said embryos and development of said embryos to plants and between 2%-4% of sucrose.

2. The process according to claim 1, wherein the concentrations of 6-benzylaminopurine are 2.2-4.4 μM in the nutrient induction medium and 0.44-2.2 μM in the plantlet growth medium.

3. The process according to claim 1, wherein the concentrations of sucrose are 9% in the nutrient induction medium and 3% in the plantlet growth medium.

4. The process according to claim 1, wherein a medium of the Murashige and Skoog (MS) type is used as the nutrient induction medium.

5. The process according to claim 1, wherein a medium of the Murashige and Skoog (MS) type containing a vitamin and amino acid supplement is used as the nutrient induction medium.

6. The process according claim 1, wherein the plantlet growth medium contains inorganic salts, vitamins and an amino acid, in quantities identical to those in the nutrient induction medium.

7. The process according to claim 2, wherein immature embryos from 4 to 21 days old and between 0.1 and 5 mm in size are cultured, and wherein said embryos having a size greater than 5 mm are cut up into several fragments capable of regeneration.

8. The process according to claim 7, wherein the cultivars T 76, RT 26, HA 290, HA 291, HA 300, HA 303 or Giant Gray Stripe are used.

9. The process according to claim 1, wherein, after step (b), the plants obtained are further cultured for root induction.

10. The process according to claim 1, wherein, after step (b), the plants bearing roots are moved to soil and incubated in a climatic chamber at 15° C. with a light intensity of 6,000 lux and a photoperiod of 15 h per day.

11. The process according to claim 1, wherein, after step (b), the plants obtained are grafted.

12. The process according to claim 1, further comprising the step of culturing the plants on a rooting medium containing an auxinic hormone thereby forming roots.

* * * * *